(12) United States Patent
Kilawee et al.

(10) Patent No.: US 6,619,051 B1
(45) Date of Patent: Sep. 16, 2003

(54) INTEGRATED CLEANING AND SANITIZING SYSTEM AND METHOD FOR ICE MACHINES

(75) Inventors: Patick Kilawee, Hugo, MN (US); Daniel Tallman, Roseville, MN (US); Quang Dao, Eden Prairie, MN (US)

(73) Assignee: Ecolab Inc., Mendota Heights, MN (US)

( * ) Notice: Subject to any disclaimer, the term of this patent is extended or adjusted under 35 U.S.C. 154(b) by 0 days.

(21) Appl. No.: 10/194,184

(22) Filed: Jul. 12, 2002

(51) Int. Cl.[7] ............................. F24F 3/16; F25G 1/18; F25G 1/00
(52) U.S. Cl. ......................... 62/78; 62/348; 62/303
(58) Field of Search ........................ 62/78, 303, 348; 134/54, 56 R, 58 R; 510/247, 253, 383, 375, 504, 434

(56) References Cited

U.S. PATENT DOCUMENTS

| | | | |
|---|---|---|---|
| 3,629,005 A | * 12/1971 | Belden | 134/171 |
| 4,147,558 A | * 4/1979 | Fraula et al. | 134/10 |
| 4,152,173 A | * 5/1979 | Jackson et al. | 134/10 |
| 4,209,343 A | * 6/1980 | Lane et al. | 134/22.12 |
| 4,258,056 A | 3/1981 | Lentsch | 424/303 |
| 4,284,653 A | 8/1981 | Shigeoka et al. | 426/312 |
| 4,295,932 A | 10/1981 | Pocius | 162/161 |
| 4,297,224 A | 10/1981 | Macchiarolo et al. | 210/755 |
| 4,324,635 A | 4/1982 | Sweeney | 204/266 |
| 4,325,934 A | 4/1982 | Swindells et al. | 423/478 |
| 4,330,531 A | 5/1982 | Alliger | 424/149 |
| 4,370,305 A | 1/1983 | Affonso | 422/292 |
| 4,376,787 A | 3/1983 | Lentsch et al. | 424/315 |
| 4,460,373 A | 7/1984 | Beavan | 8/103 |
| 4,542,008 A | 9/1985 | Capuano et al. | 423/477 |
| 4,547,381 A | 10/1985 | Mason et al. | 426/316 |
| 4,585,482 A | 4/1986 | Tice et al. | 106/15.05 |
| 4,689,169 A | 8/1987 | Mason et al. | 252/186.24 |
| 4,816,232 A | * 3/1989 | Barrau et al. | 422/301 |
| 4,832,972 A | 5/1989 | Toledo-Flores et al. | 423/327 |
| 4,878,361 A | 11/1989 | Kohl et al. | 62/352 |
| 4,907,422 A | 3/1990 | Kohl et al. | 62/352 |
| 4,908,188 A | 3/1990 | Jefferis, III et al. | 422/111 |
| 4,935,153 A | 6/1990 | Favstritsky et al. | 210/755 |
| 4,966,716 A | 10/1990 | Favstritsky et al. | 210/775 |
| 4,966,775 A | 10/1990 | Donofrio et al. | 424/661 |
| 5,014,523 A | 5/1991 | Kohl | 62/347 |
| 5,091,107 A | 2/1992 | Hutchings | 252/187.21 |
| 5,140,831 A | 8/1992 | Kohl et al. | 62/347 |
| 5,193,357 A | 3/1993 | Kohl et al. | 62/347 |
| 5,208,057 A | 5/1993 | Greenley et al. | 426/332 |
| 5,229,072 A | 7/1993 | Tarancon | 422/37 |
| 5,289,691 A | 3/1994 | Schlosser et al. | 62/78 |
| 5,360,609 A | 11/1994 | Wellinghoff | 514/772.3 |
| 5,368,815 A | * 11/1994 | Kasting, Jr. et al. | 422/3 |
| 5,382,520 A | 1/1995 | Jenson et al. | 436/55 |
| 5,408,834 A | 4/1995 | Schlosser et al. | 62/78 |
| 5,458,851 A | 10/1995 | Schroeder et al. | 422/28 |
| 5,476,579 A | 12/1995 | Choi et al. | 204/95 |
| 5,586,439 A | 12/1996 | Schlosser et al. | 62/78 |
| 5,631,300 A | 5/1997 | Wellinghoff | 514/772.3 |
| 5,639,295 A | 6/1997 | Wellinghoff et al. | 106/15.05 |
| 5,639,559 A | 6/1997 | Mason et al. | 423/472 |

(List continued on next page.)

Primary Examiner—William E. Tapolcai
Assistant Examiner—Mohammad M. Ali
(74) Attorney, Agent, or Firm—Vidas, Arrett & Steinkraus

(57) ABSTRACT

A deliming and sanitizing process which includes injecting a liquid delimer composition into a pre-mix reservoir, and substantially simultaneously injecting a second liquid sanitizing composition into a pre-mix reservoir wherein the liquid delimer composition and the liquid sanitizing composition form a mixture which is then transported from the pre-mix reservoir into a water circulation system such as in an automatic ice machine for cleaning and sanitizing the system.

21 Claims, 9 Drawing Sheets

U.S. PATENT DOCUMENTS

| | | | |
|---|---|---|---|
| 5,650,446 A | 7/1997 | Wellinghoff et al. | 514/772.3 |
| 5,695,814 A | 12/1997 | Wellinghoff et al. | 427/213 |
| 5,697,561 A * | 12/1997 | Plank et al. | 241/100 |
| 5,705,050 A | 1/1998 | Sampson et al. | 205/687 |
| 5,705,092 A | 1/1998 | Wellinghoff et al. | 252/187.21 |
| 5,707,739 A | 1/1998 | Wellinghoff et al. | 428/403 |
| 5,736,016 A | 4/1998 | Allen | 204/237 |
| 5,752,393 A | 5/1998 | Schlosser et al. | 62/303 |
| 5,787,723 A | 8/1998 | Mueller et al. | 62/347 |
| 5,788,687 A | 8/1998 | Batich et al. | 604/890.1 |
| 5,853,689 A | 12/1998 | Klatte | 423/478 |
| 5,878,583 A | 3/1999 | Schlosser et al. | 62/73 |
| 5,888,528 A | 3/1999 | Wellinghoff et al. | 424/405 |
| 5,914,120 A | 6/1999 | Wellinghoff et al. | 424/406 |
| 5,922,776 A | 7/1999 | Wellinghoff et al. | 514/772.3 |
| 5,953,925 A | 9/1999 | Mueller et al. | 62/73 |
| 5,965,264 A | 10/1999 | Barenberg et al. | 428/402 |
| 5,967,202 A | 10/1999 | Mullen et al. | 141/104 |
| 5,974,810 A | 11/1999 | Speronello | 62/66 |
| 5,980,826 A | 11/1999 | Barenberg et al. | 422/37 |
| 5,984,993 A | 11/1999 | Mainz et al. | 71/12 |
| 6,004,439 A | 12/1999 | Bakhir et al. | 204/260 |
| 6,039,220 A * | 3/2000 | Jablonski et al. | 222/236 |
| 6,044,852 A * | 4/2000 | Epperson et al. | 134/56 R |
| 6,046,243 A | 4/2000 | Wellinghoff et al. | 514/772.3 |
| 6,071,483 A | 6/2000 | Pastore | 422/255 |
| 6,071,539 A | 6/2000 | Robinson et al. | 424/466 |
| 6,077,495 A | 6/2000 | Speronello et al. | 423/477 |
| 6,134,907 A | 10/2000 | Mueller et al. | 62/351 |
| 6,171,558 B1 | 1/2001 | Simpson | 422/186.3 |
| 6,196,007 B1 | 3/2001 | Schlosser et al. | 62/73 |
| 6,238,643 B1 | 5/2001 | Thangaraj et al. | 423/477 |
| 6,324,863 B1 * | 12/2001 | Henry | 62/347 |
| 6,334,328 B1 * | 1/2002 | Brill | 62/347 |
| 6,478,034 B1 * | 11/2002 | Durth et al. | 134/22.18 |

* cited by examiner

INTEGRATED CLEANING AND SANITIZING SYSTEM AND METHOD FOR ICE MACHINES

FIELD OF THE INVENTION

The present invention relates to a dual cleaning and sanitizing system useful in icemaking machines which allows deliming and sanitizing simultaneously.

BACKGROUND OF THE INVENTION

Automatic ice makers run essentially continuously using two basic systems. These systems are the coolant/recycle refrigerant system and the water/ice system. The water/ice system of ice making machines typically includes a water supply, a water reservoir or sump, drain valves from the sump to a line draining to the drain or sewer, a water circulation mechanism, a water distribution means, and appropriate connecting lines. Water is distributed across an ice forming mold, or evaporator plate, and ice is formed thereon. The water which is not frozen flows down the plate into a water container and is returned to the water sump. The ice formed as required is harvested and falls into the ice bin.

Circulating water can lead to the build up of certain deposits on metal surfaces in the water/ice system. In particular, build-up of water hardness chemicals, such as magnesium and calcium salt, can impede water flow and thus the operation of ice making machines, particularly ice making machines running automatically for extended periods of time.

Particularly prone to build up of these deposits are the surfaces of the water sump, the internal surfaces of connecting lines from the sump to the circulating pump and through the circulating pump to the distributor, the distributor itself, and particularly the evaporator plate or ice molding surfaces or fins designed in the ice-forming trays made a part of the evaporator plate and in close proximity or attached directly to the evaporator external surfaces.

Water hardness chemicals have more of a tendency to build up on certain surfaces such as in the water sump where the solenoid drain valve may be activated to drain water periodically. Water containing these or other undissolved salts has a tendency to freeze at lower temperatures than pure water. Water containing higher levels of salts may form what is known in the art as "white ice." White ice not only looks bad, it may also taste bad as well. Fresh water which inhibits the formation of "white ice" can be recharged to the water/ice system.

Accumulation of other deposits in addition to water hardness chemicals is also of concern during extended use of automatic ice machines including accumulation of soils, dirts, dusts, and formation and accumulation of various biological deposits such yeasts, algae, molds, fungi, slimes, and other microbiological growths. Such fouling problems in the water-ice system can decrease efficiency and require down-time for maintenance and cleaning.

The formation and build up of such deposits not only impedes the flow of water, but it may result in increased corrosion of metal surfaces, inhibit heat transfer efficiencies particularly on the evaporator plates and ice forming molds, and generally cause poor operation of the ice maker. Thus, periodic cleaning and sanitizing of the water-ice system surfaces in order to maintain proper ice making operations.

Cleaning processes typically involved dismantling the portions of the ice making machine containing the soiled surfaces and washing and scrubbing the surfaces using acidic cleaner compositions. Use of acidic cleaners further required careful and extensive rinsing of the surfaces to avoid contact with ice later formed. Once the cleaning/rinsing was complete, then the machine must be reassembled to its usable state. The cleaning process is therefore labor intensive, costly and inefficient.

U.S. Pat. No. 5,289,691 describes a self-cleaning self-sterilizing ice making machine that has a coolant/refrigerant system, a water-ice system, a cleaning/sterilizing system and a microprocessor operated control system interconnecting the above systems.

SUMMARY OF THE INVENTION

The present invention relates to an improved, novel cleaning and sanitizing system in which both cleaning, i.e. deliming, and sanitizing can occur substantially simultaneously using a single system.

The dual liquid deliming and sanitizing system of the present invention may be employed for cleaning and sanitizing any water circulation system which includes a first product container including a liquid cleaning composition, a second product container including a liquid sanitizing composition, a pre-mix reservoir having an exit port which is in fluid communication with the water circulation system and a device in fluid communication with the first container and the second container configured and arranged for transporting liquid from the first and second containers to the pre-mix reservoir. The liquid deliming composition and the liquid sanitizing composition form a mixture in the reservoir. In the case of a reactive system in which a sanitizer is formed, the pre-mix reservoir allows the reaction to proceed a rate fast enough for integration with an automatic cleaning cycle.

In one particular embodiment, the pre-mix reservoir has an exit port which drains into a sump such as in an automatic ice making machine.

More particularly, the present invention relates to a deliming and sanitizing process for an ice machine having a water flow system, a sump and a drain, and having a headspace within the interior accessible to the interior of the machine including the steps of injecting an acidic delimer composition into the sump and injecting a sanitizing composition into the sump. This can be more advantageously accomplished by injecting the delimer composition and the sanitizer composition into a pre-mix reservoir prior to transportation into the sump. From the sump, the mixture then cycles through the water flow system.

In some embodiments, a metal chlorite composition, a metal hypochlorite composition, a quaternary ammonium composition, an acid-anionic composition, a peracetic acid composition is added to an acidic delimer in the system. Ozone generating compositions may also be employed.

In one particular embodiment of the present invention, a metal chlorite composition is added to an acidic delimer composition which forms chlorine dioxide.

The present invention advantageously allows sanitizing and deliming simultaneously in a liquid phase, and in some embodiments also allows for gaseous sanitization of the head space of a chamber or vessel, such as the head space in an ice making machine.

The dual liquid deliming and sanitizing system of the present invention may be integrated with and employed for cleaning and sanitizing any automatic water circulation system. The dual liquid cleaning and sanitizing system is easily integrated with an automatic ice making machine, for example.

For maximum benefit, the device and method of the present invention may be employed in combination with a device as described in commonly assigned copending patent application, attorney docket number E14.2-9970, DEODORIZING AND SANITIZING EMPLOYING A WICKING DEVICE incorporated by reference herein in its entirety.

DETAILED DESCRIPTIONS OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

In general, the present invention provides an improved dual deliming/cleaning system readily integrated with an automatic ice making machine, for example. The present invention includes a dual liquid dispenser in communication with the water/ice system of the automatic ice making machine. In general, the system has the capability of electronically monitoring and controlling the various cycles of the ice making process. The dual deliming/cleaning system of the present invention is easily integrated with any automatic ice making machine.

The dual deliming/cleaning system, in general, includes at least one container for a liquid delimer composition, at least one container for a liquid sanitizer composition, and at least one injection mechanism, such as a pumping device, for injecting the delimer composition and the sanitizer composition substantially simultaneously into the sump of the ice making machine, or in the case of a reactive system, more suitably into a pre-mix reservoir which will be described in detail below.

"Cleaning" may refer to the removal of both non-biological and biological deposits and debris. Cleaning is primarily accomplished through the use of an acidic product to remove hard water components and other mineral incrustations.

"Sanitizing" may refer to the reduction in the population of biological microorganisms and is typically measured as a log kill.

Figure 1:
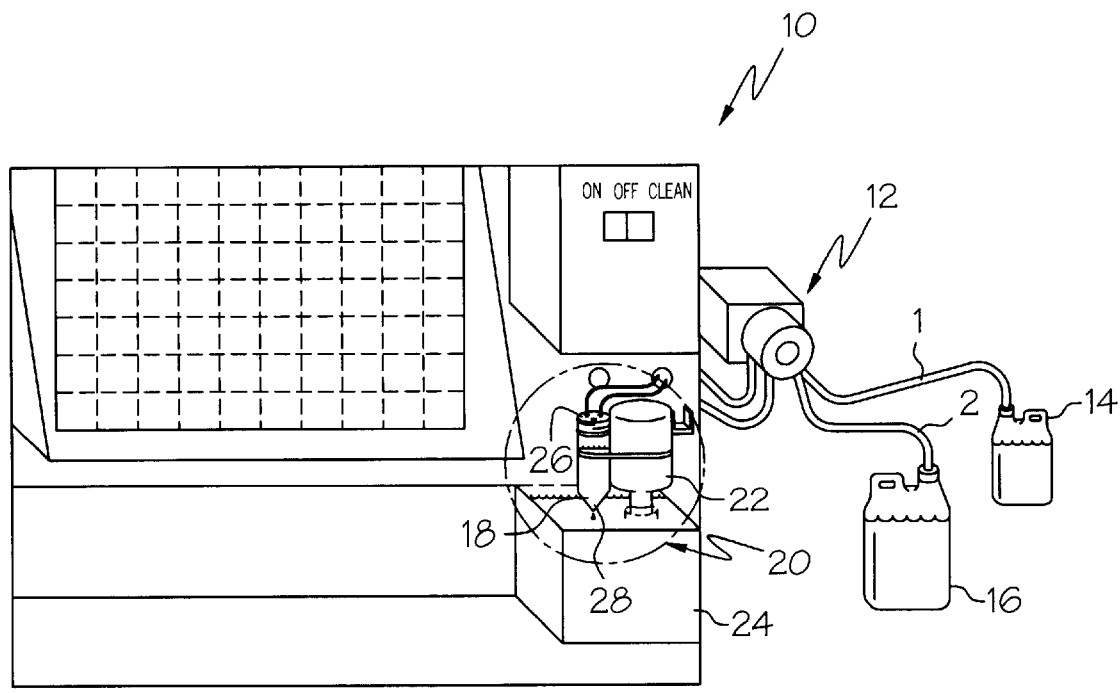
FIG. 1 illustrates an automatic ice making machine having the dual liquid cleaning and sanitizing system of the present invention.

FIG. 1 illustrates generally at 10, an automatic ice making machine with which one embodiment of the dual liquid deliming/sanitizing system of the present invention is employed. As shown in FIG. 1, a first container 14 having a first deliming composition is in fluid communication with a dual liquid injection mechanism 12, for example, a dual liquid pump, and a second container 16 having a second liquid sanitizer composition is in fluid communication with the same injection mechanism 12. Alternatively, two separate injection mechanisms may be employed.

Injection mechanism 12 transports liquid delimer from container 14 and liquid sanitizer from container 16 into a common pre-mix reservoir 18 which is in fluid communication with the sump 24 of the automatic ice machine 10. In this particular embodiment, pre-mix reservoir 18 has an exit port 28 which drains into the sump 24. Alternatively, the pre-mix reservoir 18 may be in fluid with the sump 24 via a conduit (not shown) for example. A pump may be alternatively employed to transport the fluid from the pre-mix reservoir as well.

From the sump 24, the mixture of delimer/sanitizer is cycled through the ice machine water circulation system by a recirculation pump 22. The mixture may be transported from reservoir 18 either through the use of gravity wherein the mixture drains from an exit port 28 at the bottom of the reservoir 18 into the sump 24, and is then cycled through the ice machine during the cleaning cycle, or optionally, it may be injected into the sump 24 through the use of an injection mechanism. The rate of entrance of the delimer/sanitizer from containers 14, 16 may be controlled by an electronic controller (not shown), for example, which is integrated with the ice machine 10. The electronic controller may reside in the dual-liquid pump or in the ice machine, or may partially reside in the dual-liquid pump and in the ice machine. In a typical arrangement, dosage is determined by the pump speed which is fixed, the pump displacement per cycle which is fixed, and the run-time which is field-adjustable.

For example, the ice machine controller activates a cleaning cycle after a preset time or a preset number of ice harvests. Ice production is halted and a sequence of cleaning and rinsing steps takes place. During the washing step, the ice machine controller sends an electronic signal to the dual-liquid pump controller to activate dispensation of the products. The run time of the dual-liquid pump is controlled by the electronics in the dual-liquid pump and is typically field-adjustable.

The electronic control system may be programmed such that the water fill valves and sump drain valves are opened/closed for set amounts of time. The electronic controller may be further equipped with a fail-safe feature which may automatically stop dispensing of delimer/sanitizer to prevent an overflow of the mixture from reservoir 18. Alternatively, alarm systems may also be employed.

Alternatively, as described above, reservoir 18 may be equipped with another additional injection mechanism (not shown) which injects the mixture into the automatic ice machine water circulation system.

In one embodiment of the present invention, the first container 14 has an acidic deliming composition such LIME-A-WAY available from Ecolab, Inc. in St. Paul, Minn., and the second container 16 has a sodium chlorite sanitizing composition. An excess amount of acid is transported along with the sodium chlorite from containers 14, 16 through conduits 1 and 2 consecutively by injection mechanism 12 into a pre-mix reservoir 18 where a reaction begins between the sodium chlorite and the acid wherein chlorine dioxide gas is produced. This reaction may be represented by the following general formula:

$$5\ NaClO_2 + (4/n)H_nX = 4ClO_2 + NaCl + (4/n)Na_nX + 2H_2O$$

Reservoir 18 has an exit port which allows the liquid mixture, which in this embodiment has already begun reacting, to drain into the sump 24 of the ice making machine 10. The liquid mixture exits reservoir 18 at one rate and the first and second compositions enter reservoir 18 at another rate such that the reservoir does not overflow at the top 26. Chlorine dioxide gas also escapes from the sump into the head space of the ice making machine where it acts as an antimicrobial agent. This allows the antimicrobial agent to reach non-wetted surfaces of the ice making machine which are not otherwise easily accessible. Furthermore, they are not reachable through the use of the automatic liquid deliming/sanitizing system. This is therefore an added benefit to employing a deliming/sanitizing system which also generates an antimicrobially active gas.

Figure 2:
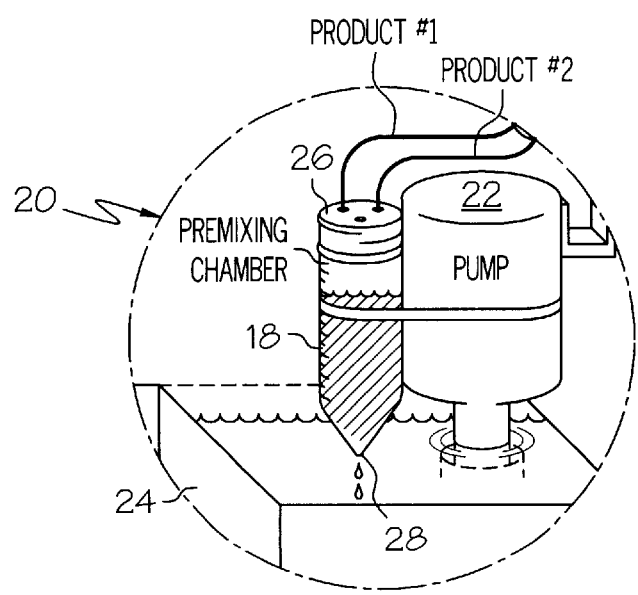
FIG. 2 illustrates an enlarged view of part of the dual liquid and cleaning system of the present invention.

The pre-mix reservoir has been found to be particularly useful where reactive systems are employed to produce a sanitizing composition in order to ensure a rapid enough reaction rate once the cleaning cycle has been initiated. FIG. 2 is an enlarged version of the reservoir of the present invention which is also shown at 20 in FIG. 1.

A refinement of the reservoir 18 is to design it such that it drains partially, leaving a small amount of the liquid mixture to prolong the release of chlorine dioxide into the head space. The reservoir could be gradually filled with small increments of the two liquid products to more or less give a sustainable dosage of chlorine dioxide into the head space between the periodic treatments of the sump.

The dispensing device of the present invention may be any dispenser capable of dispensing at least two liquids. Liquids are desirable because they are easily dispensed from an automatic dispensing unit, removing the need for manual dispensing. The dispensing of the liquids may be accomplished through the use of more than one single injection mechanism, i.e. pumping mechanism, and more suitably a dual liquid injection system.

The injection mechanism of the dispenser may be in the form of a positive displacement pump such as a gear pump, an oscillating pump, a screw pump, a syringe pump, a piston pump, a peristaltic pump, and so forth, for instance.

From the sump 24 as shown in FIG. 1, the now dual liquid cleaning and sanitizing mixture is carried through the normal cycle of the ice making machine 10. The dispenser of the present invention is easily integrated with and may be used in combination with any automatic ice making machine. Examples of automatic ice making machines are described in U.S. Pat. No. 4,907,422, U.S. Pat. No. 4,878,361, U.S. Pat. No. 5,014,523, U.S. Pat. No. 5,140,831, U.S. Pat. No. 5,193,357, U.S. Pat. No. 5,289,691, U.S. Pat. No. 5,408,834, U.S. Pat. No. 5,586,439, U.S. Pat. No. 5,752,393, U.S. Pat. No. 5,787,723, U.S. Pat. No. 5,878,583, U.S. Pat. No. 5,953,925, U.S. Pat. No. 6,134,907 U.S. Pat. No. 6,196,007, and so forth each of which is incorporated by reference herein in their entirety. These ice machines, and the description herein, are intended for exemplary purposes only and one of skill in the art will recognize that modifications of these designs as well as other designs will also be compatible with the present invention without departing from the scope of the present invention.

Automatic ice making machines useful herein may include a coolant/refrigerant system, a water/ice system, and the deliming/sanitizing system of the present invention in communication with the water/ice system. In broad terms, the coolant recycle refrigerant system includes a compressor, a condenser, an expansion valve, an evaporator and interconnecting lines. The water/ice system includes a water flow system, a sump, and a drain or overflow system for discarding excess water from the circulating water system. The machine also has a headspace within the interior for access to the interior of the ice machine.

The water/ice system further includes a means of circulating water through the system such as a pump, and a means for distributing the circulating water across the molds or evaporator plate such as a water distributor. The systems may include various other parts not specifically described herein for operation of the systems.

Further, the ice making machines of the present invention may include an electronic controlling and monitoring system which is capable of operating the coolant/refrigerant system, the water/ice system and the deliming/sanitizing system. The electronic controlling and monitoring system is capable of initiating and controlling several cycles including ice making, ice harvesting, and deliming/sanitizing. In general, the electronic controlling and monitoring system may include a microprocessor, a control panel and a power supply or access thereto. This monitoring system may further be equipped for alerting system readiness and system operation, including a dispenser alert for indicating levels of cleaner/sanitizer and when the addition of more is required.

The control of the dual-liquid system of the present invention may be distributed between the ice machine and the electronics of the dispenser. Thus, the electronic controlling/monitoring system of the ice making machine may also be programmed to control the dispensing system, or the dispensing system may have its own electronic controlling/monitoring system.

For example, the combination may include a "smart" dispenser/ "dumb" ice machine. In this embodiment, the primary function of the ice machine is to control the production of ice and may include analog relays and such. For such a system, the dispenser of the present invention may have its own controller/microprocessor. The dosing of the chemical compositions may thus be controlled by the microprocessor/controller of the dispenser itself and activation of various relays may indicate the state of operation. The microprocessor/controller of the dispenser in this embodiment may be programmed to halt ice production and initiate the cleaning cycle. The ice machine may be manually controlled to place the machine in the cleaning cycle but this is less convenient because cleaning cannot be initiated automatically.

Another combination includes a "dumb" dispenser and a "smart" ice machine. In such an embodiment, the microprocessor/controller of the ice making machine monitors ice production, may include its own internal diagnostics, and can initiate an automatic cleaning cycle during which ice production is halted. In such a system, the microprocessor sends a signal to the dispenser indicating when to dispense the cleaning and sanitizing compositions and how much to dispenser. The signal may be adjustable as to voltage, length of dispensing, and so forth. Thus, the microprocessor basically will indicate how long the pump(s) of the dispenser should be running.

A third combination is one in which the automatic ice making machine initiates its own cleaning cycle and has a "fixed" duration signal for dispensation of cleaning/sanitizing compositions. The dual liquid dispensers of the present invention may be provided with variable speed pumps, a timer which is adjustable for controlling the length of time the pump is on for dispensation of product, and countdowns on the dispensing cycles for detection/calculation when the dispenser requires addition of more product. An example of such an ice making machine is found in U.S. Pat. No. 5,289,691.

The dual liquid cleaning/sanitizing system of the present invention advantageously incorporates a fail-safe system which may be controlled in any way described above in order to prevent the occurrence of over-dispensing, particularly into the reservoir and/or sump. This may involve the addition of a remote alarm such as one employing radio frequency or similar method, which is further capable of network communication, and which may be integrated into the system as well such as through integration with the circuitry of the machine, through the use of an add-on box to the dispenser, or integrated into the ice machine controller.

In a system in which chemicals are being dispensed, a fail-safe system is desirable to prevent the occurrence of over-dispensing, particularly into the reservoir or the sump. Furthermore, an alarm system may be desirable to notify the system operator of an overdosing.

In addition to electronic fail safe devices, it is advantageous to limit pump injection rates such that there is no possibility of overflowing the sump, to to limit the size of the containers which hold the chemical compositions so that the chemicals may be exhausted prior to completion of the rinsing cycles.

In one embodiment of the present invention, the dual deliming/sanitizing system is employed in combination with an automatic ice making machine as described in U.S. Pat. No. 5,289,691 incorporated by reference herein in its entirety. In this embodiment, the dispenser of the present invention may be integrated with the automatic ice making machine by "plugging" the dispenser in to the circuitry of the ice making machine, the dispenser being in fluid communication with the water/ice system.

Figure 5:
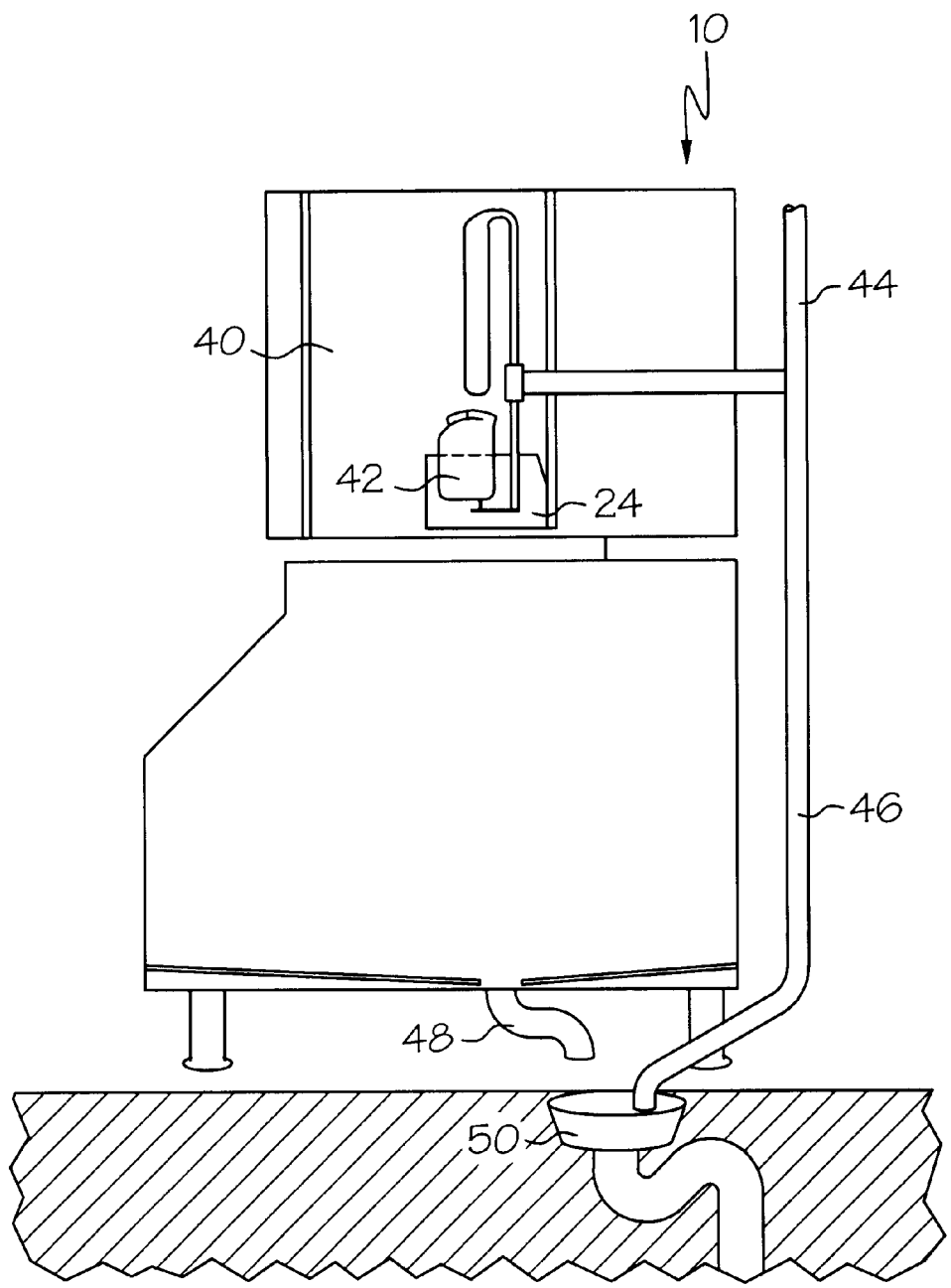
FIG. 5 is a side view of an automatic ice making machine having a typical drain configuration.

Another problem associated with the use of automatic ice making machines is that mold and mildew can plug both the drain for the ice bin, as well as the floor drain. The present invention may be employed to treat both drains to reduce the build-up of mold and other fungi. FIG. 5 shows generally at 10 a typical configuration for an ice machine in which the ice bin drain 48 drains separately from sump drain line 46. The sump has a recirculating/drain pump 42. Both ice bin drain 48 and sump drain line 46 drain into floor drain 50.

Figure 6:
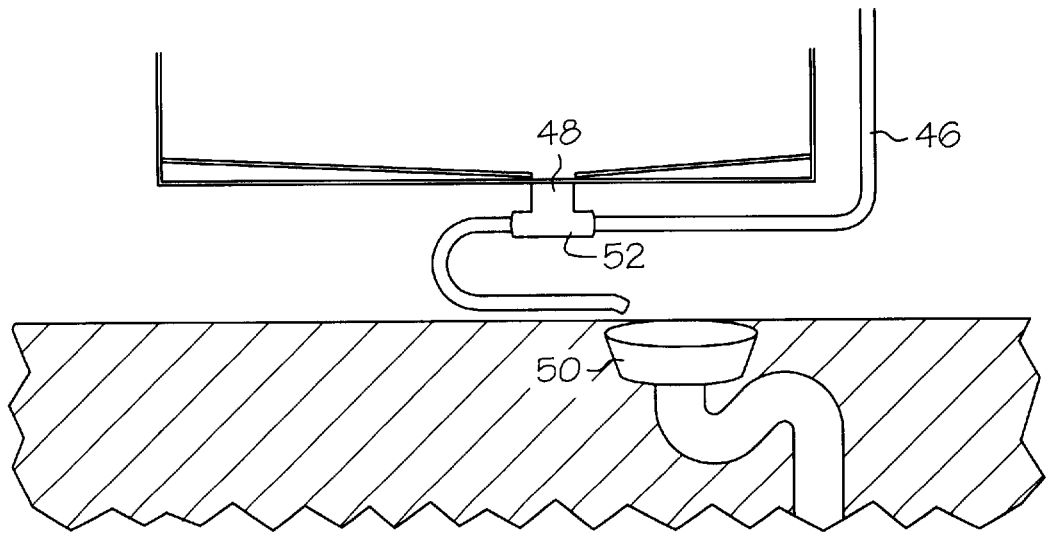
FIG. 6 is an expanded view of a modified drain configuration for an automatic ice making machine.

FIG. 6 shows an expanded alternative configuration for the drain system in which both the ice bin drain 48 and the sump drain line 46 are fed to the same tee connector 52 which then drains into floor drain 50.

Figure 7:
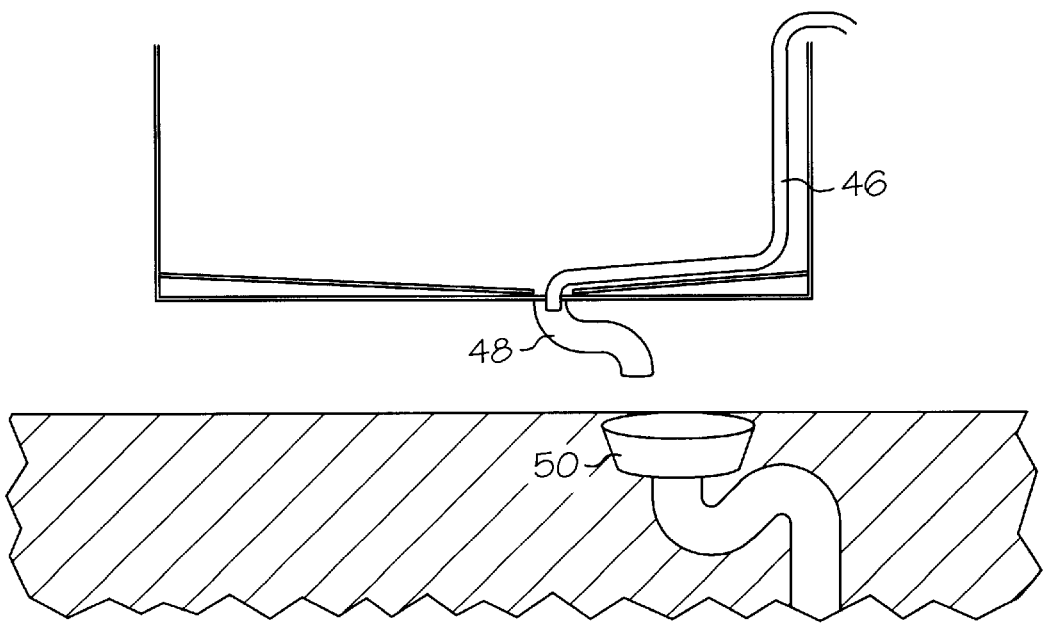
FIG. 7 is an expanded view of an alternative embodiment of a drain configuration for an automatic ice making machine.

FIG. 7 shows yet another alternative configuration for the drain system of the automatic ice making machine 10 in which the sump drain line 46 is fed directly into the ice bin drain 48 which then drains into the floor drain 50. In any of the above described configurations, the deliming/sanitizing method of the present invention provides treatment for each drain.

The cleaning/sanitizing composition may be any composition which includes both a deliming or cleaning composition and a sanitizing composition. Suitably, the delimer is acidic in nature.

Examples of useful delimers include, but are not limited to, phosphoric acid, sulfuric acid, hydrochloric acid, citric acid, and so forth. Phosphoric acid is suitable for use because it is less hazardous for contact with food. An example of a commercially available delimer is LIME-A-WAY®, a phosphoric acid based delimer available from Ecolab, Inc. located in St. Paul, Minn.

Examples of useful sanitizing compositions include a metal chlorite composition, a quaternary ammonium composition, peracetic acid composition, and so forth.

In some embodiments, an acid delimer and a metal hypochlorite are utilized to produce chlorine dioxide. Using this system, an excess of the acid component is used for deliming, and it assures that both acid and chlorine dioxide are present in the cleaning/sanitizing system. Acids have been found to be excellent for deliming and chlorine dioxide is an excellent sanitizer. Examples of metals utilized in combination with the chlorite include the alkali metals and alkaline earth metals such as sodium or potassium. The metal chlorite may then be injected resulting in a reaction which produces chlorine dioxide in the presence of water according to the following general formula as described above:

$$5\,NaClO_2+(4/n)H_nX \rightarrow 4ClO_2+NaCl+(4/n)Na_nX+2H_2O$$

where X is any acid anion.

Chlorine dioxide is particularly useful because it partitions itself in both the gas phase and the liquid phase. Chlorine dioxide partitions at a ratio of about 5 ppmv (partial volume) in air and about 1 mg/liter in water under cold water conditions. This partitioning effect allows for sanitization of areas that are difficult to reach with a liquid, i.e. the non-wetted areas. For instance, in an ice machine, the cleaner/sanitizer is circulated through the ice-making unit. However, due to the high humidity and temperature, mold, yeast, fungi, and other microbes may build in the upper unit where no cleaning composition reaches. Using this system, chlorine dioxide gas will reach these upper areas, while the liquid cleans the ice making unit below. Such partitioning makes chlorine dioxide particularly suitable to sanitize the head space of an ice machine, for instance, at a concentration that is also suitable for sanitizing/disinfecting the water in the sump.

The acid required for effective deliming typically may be in substantial molar excess of the sodium chlorite. The acid dosage is dictated primarily by what is required to remove hard water components and other mineral buildup; and reaction with the sodium chlorite to form chlorine dioxide is a secondary consideration.

The acid and sodium chlorite dosing can be set to deliver about 100 to about 200 ppm available chlorine dioxide (total oxychloro species as chlorine dioxide) so as to comply with FDA requirements for sanitizing solutions used for food processing equipment and food contact surfaces as set forth in 21 CFR 178.1010(b)(34) and (c)(29).

In other embodiments, a combination of an acidic delimer and sodium hypochlorite are employed to generate chlorine gas which is also an effective sanitizer.

For systems in which at least two chemical concentrates are being mixed to produce a reactant, a reservoir has been advantageously employed. The two chemical concentrates are fed into the reservoir where the reaction begins. Using a reservoir in this manner has been found to produce a more quickly produce an effective amount of reaction product. If, in an ice making machine, for instance, the chemical concentrates are fed directly into the sump, the water in the sump immediately dilutes the reactants which results in a slower reaction time.

Figure 3:
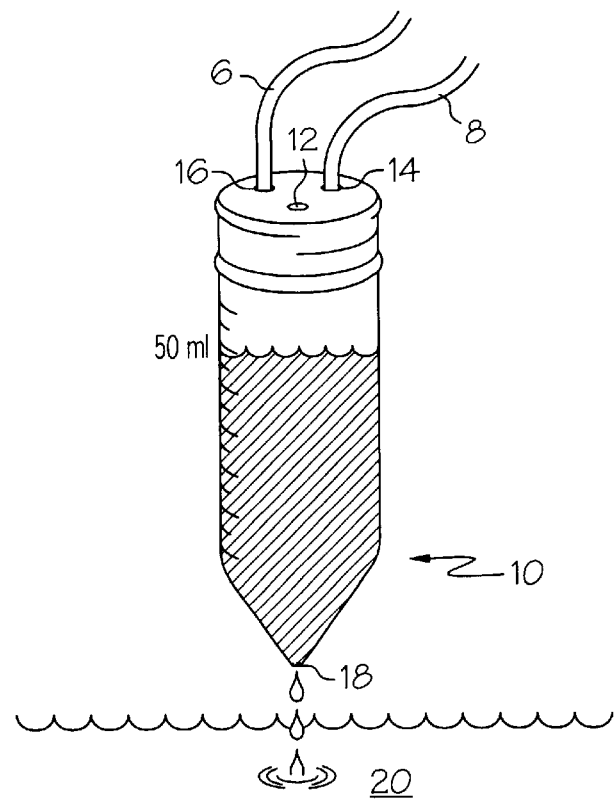
FIG. 3 illustrates a reservoir of the present invention.

FIG. 3 illustrates generally at 10, one example of a reservoir of the present invention. Conduit 6 transports the delimer composition into the reservoir while conduit 8 transports the sanitizer composition. There is also a vent 12 which allows the escape of any gas which may be produced as a result of the reaction such as chlorine dioxide or chlorine gas. Reservoir 10 also has an opening in the bottom of the reservoir which allows the now reacting delimer/sanitizer composition to flow into another vessel 20, such as the sump of an ice machine. The reaction continues to proceed in the secondary vessel 20.

Figure 4:
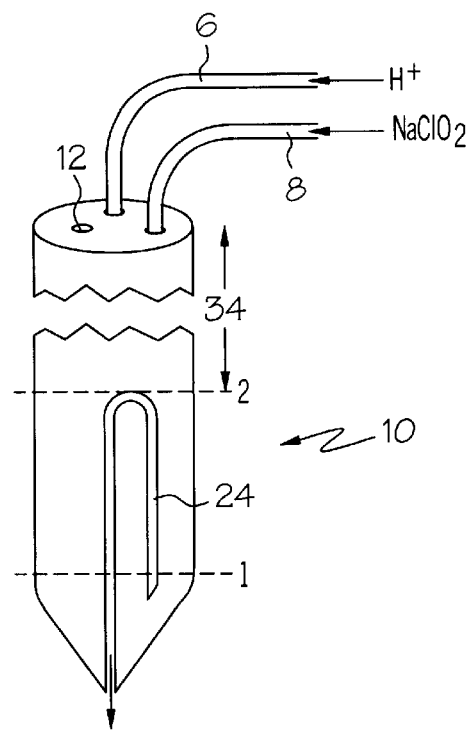
FIG. 4 illustrates an alternative embodiment of the reservoir according to the present invention.

FIG. 4 shows generally at 10, an alternative embodiment of a reservoir of the present invention in which a siphon tube 32 is employed to transfer product from the reservoir 10 to the sump 24 shown in FIG. 1. Again, there are two conduits 6, 8 through which the acidic composition and the metal chlorite composition may be transferred into the pre-mix reservoir 10. As chlorine dioxide gas is produced from the reaction, it may be vented through vent hole 12, and into the head space of, for example, an ice machine. Using such a siphoning device typically requires a minimum level 1 of liquid and a maximum level of liquid 2 as well as a free board volume 34. Once the level of liquid reaches 2, the mixture will siphon out through siphon tube 32. The solution will continue to siphon until it reaches liquid level 1. The free board volume 34 should be maintained large enough to hold a complete dosage. Small increments of the reactants may be added between liquid levels 1 and 2.

This device may be equipped with an electronic monitoring system, or may be "plugged into" the electronics of an automatic ice making machine, for example. When the cleaning cycle is on, and addition to the sump is required, larger volumes of reactants can be automatically triggered through the use of the electronic/monitoring system as described above. When the cleaning cycle is off, and the level of liquids in the reservoir has reached level 1, the addition of reactants from the product containers may be stopped by the electronic monitoring/control device.

The device may be employed in any small area where deodorizing is desired such as athletic lockers, food storage containers, walk-in freezers, storage closets such as those for cleaning products, and so forth.

In embodiments in which the combination of delimer/sanitizer is an acid component and sodium chlorite, or an acid component and sodium hypochlorite, the reservoir is advantageously used. This does not, however, exclude situations in which the acid delimer/sanitizer are fed directly into the sump.

The areas and surfaces of the ice making machine that actually come into contact with the water/ice, i.e. the wettable areas, are relatively easy to clean, particularly with an automatic cleaning/sterilizing system.

However, the areas and surfaces of the ice making machine that do not come into contact with the water/ice, i.e. the non-wettable areas, such as the head portion of the ice machine, are relatively difficult to clean. Typically, the front panel of the head portion would have to be removed and the surfaces scrubbed by hand. Cleaning corners can be a challenge and quite time consuming, and the parts located in the head portion of the ice machine, such as the pump, also make cleaning more of a challenge. The presence of gaseous sanitizer such as chlorine dioxide or chlorine in the head space of the ice making machine can therefore decrease the amount of manual cleaning required for the head portion.

A typical sump for a commercial ice machine is 4 to 10 liters and the head space is approximately 50–60 liters. The amount of sodium chlorite required for injection into the sump of the ice making machine is suitably about 0.5 to about 5 grams of sodium chlorite and more suitably about 0.7 g to about 3.5 g, about 10 ml to about 50 ml or a 6.5% solution, or about 1 ml to about 15 ml and more suitably about 2 ml to about 11 ml of a 25% solution. This is based on a 100–200 ppm compliance, a reaction which is about 80% complete, conversion of $ClO_2$ to $NaClO_2$ and about 4 to about 10 liter volumes. Thus, these ranges may vary based on the conditions present. As the amount of sodium chlorite is varied between about 6% and about 25% at a constant dosing, the amount of chlorine dioxide present in the head space of the ice machine is about 5 to about 40 ppmv and the amount of chlorine dioxide present in the sump of the ice machine is about 2 to about 10 ppm.

The dual deliming/sanitizing device and method of the present invention may be employed in combination with any system which includes water circulation such as ice making machines, steamers, deodorizers, proofers for holding bread dough and thawing meat, ice flakers, ice conveying systems, dairy and beverage tanks and pipelines, beverage dispensers, combination beverage/ice dispensers, and so on and so forth.

As described above, the present invention may be employed in combination with a device and method as described in commonly assigned copending patent application, attorney docket number E14.2-9970, DEODORIZING AND SANITIZING EMPLOYING A WICKING DEVICE incorporated by reference herein in its entirety.

The above disclosure is intended for illustrative purposes only and is not exhaustive. The present invention may find utility in any system in which a water circulation system requires cleaning and sanitizing.

The embodiments described therein will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The following non-limiting examples further illustrate the present invention.

EXAMPLES

Example 1

Figure 8:
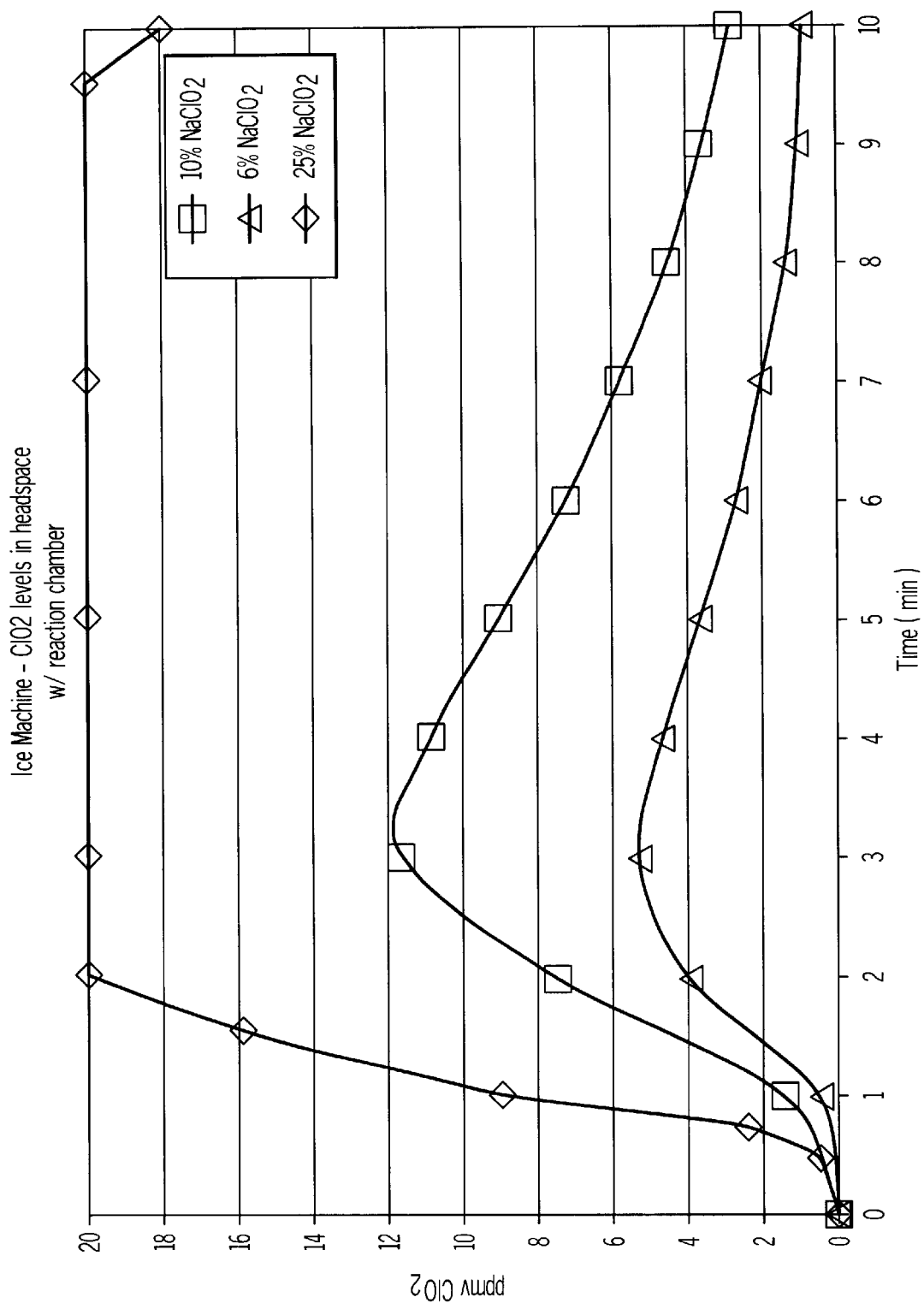
FIG. 8 is a graph showing the concentration of chlorine dioxide in the head space of an ice making unit varying the amount of sodium chlorite employed, and using a pre-mix or reaction chamber according to the present invention.
Figure 9:
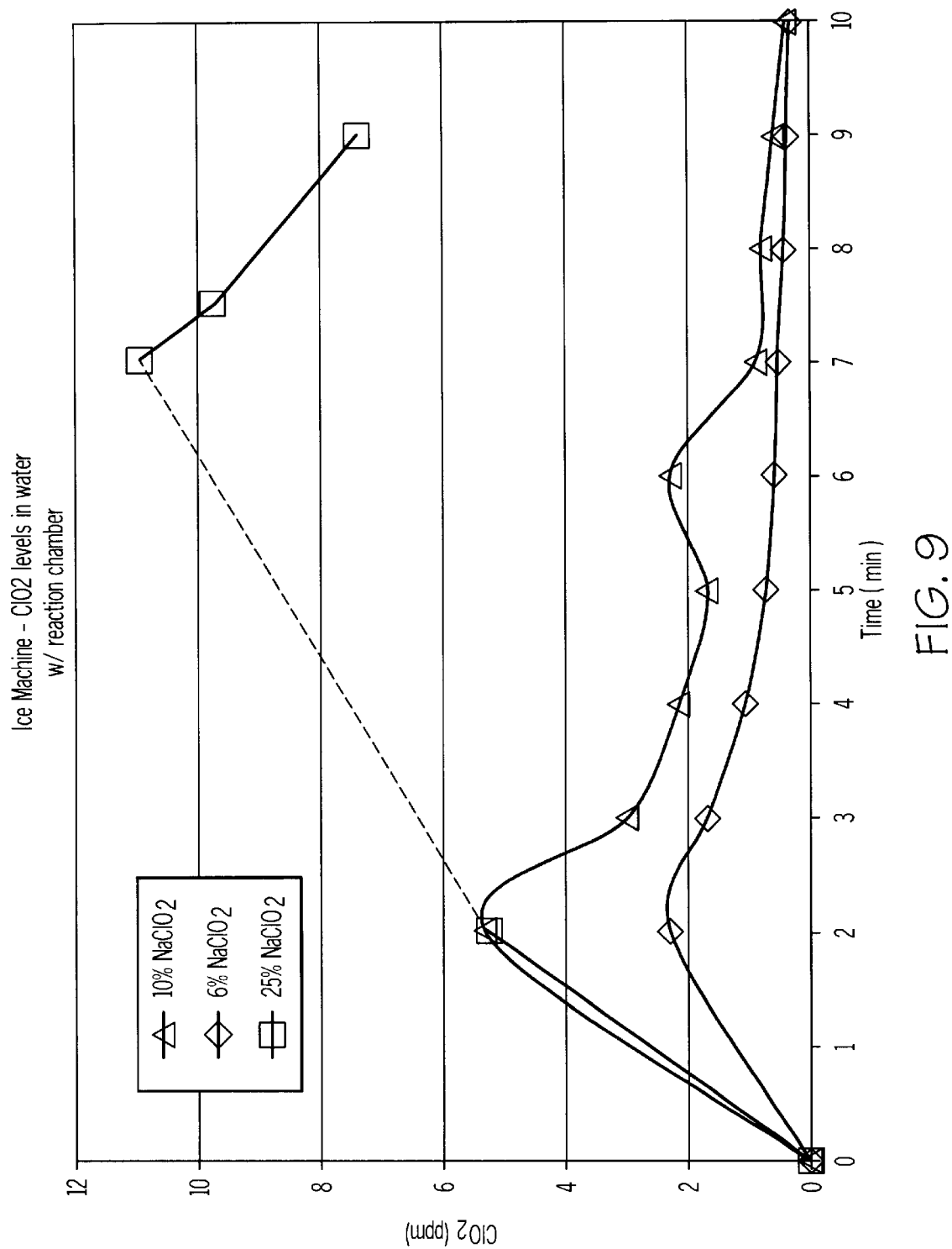
FIG. 9 is a graph showing the concentration of chlorine dioxide in the sump of an ice making unit as the amount of sodium chlorite is varied, and employing a pre-mix or reaction chamber according to the present invention.

Lime-A-Way, a phosphoric acid/citric acid based commercially available delimer and solutions of sodium chlorite were simultaneously dispensed over a one minute interval into a 150 ml pre-mix or reaction placed inside a Manitowoc automatic ice making machine. The amount of Lime-A-Way (95 ml) and the amount of sodium chlorite (13 ml) were held constant. Three separate tests were run using concentrations of 6, 10, and 25% active sodium chlorite. The pre-mix chamber had a ¹⁄₁₆" diameter drain hole to restrict outflow and provide greater generation of chlorine dioxide by allowing reaction to occur at high concentration in the product, i.e. reactant, mixture before being diluted in the sump. From the reaction chamber, the mixture drained directly to the sump of the ice making machine. The amount of chlorine dioxide was then measured in both the head space and the sump of the ice machine. The concentration of chlorine dioxide measured in the head space is found in FIG. 8 while FIG. 9 illustrates the amount of chlorine dioxide measured in the sump as the amount of sodium chlorite added was varied.

Example 2

Chlorine dioxide levels were tested in an Manitowoc automatic ice making machine by dispensing two liquids (95 ml LIMEAWAY and 13 ml chlorite(6% chlorite solution)) over one minute, (1) directly into the sump and (2) into a 150 ml reservoir or reaction chamber according to Example 1. The results of the chlorine dioxide generation are found in table 1 below. The reaction chamber allows greater amounts of chlorine dioxide to be released into the head space.

TABLE 2

| Time | Supplied Directly to Sump $ClO_2$ in Air (ppm) | Supplied to Premix Chamber $ClO_2$ in Air (ppm) |
| --- | --- | --- |
| 1 | 1 | 1 |
| 1.5 | 1.5 | 1.27 |
| 2 | 1.48 | 4.72 |
| 3 | 1.32 | 5.6 |
| 3.5 | 1.16 | 5.66 |
| 4 | 1.07 | 4.95 |
| 5 | 0.95 | 4.06 |
| 5.5 | 0.84 | 3.63 |
| 6 | 0.8 | 3 |
| 6.5 | 0.73 | 2.85 |
| 7 | 0.73 | 2.33 |
| 8 | — | 1.47 |
| 9 | 0.63 | — |
| 9.5 | 0.65 | — |
| 10 | 0.59 | 1.11 |

The data in Table 2 illustrates the concentration of chlorine dioxide in air when the delimer/metal chlorite composition are supplied directly to the sump in contrast to the concentration of chlorine dioxide in air when the delimer/metal chlorite composition are first directed to a premix chamber according to the present invention. As can be seen from the data found in Table 2 and from FIG. 10 the concentration of chlorine dioxide is slightly higher initially than when adding the sanitizer/delimer directly into the sump. This is due to the delay, when employing the pre-mix chamber, before the liquids are transferred into the sump where the mixture is then recirculated over the evaporator plate. However, because the generation of chlorine dioxide is faster under more concentrated conditions, after two minutes the headspace concentration is 2–5 times greater when the premix chamber is used.

Example 3

Figure 11:
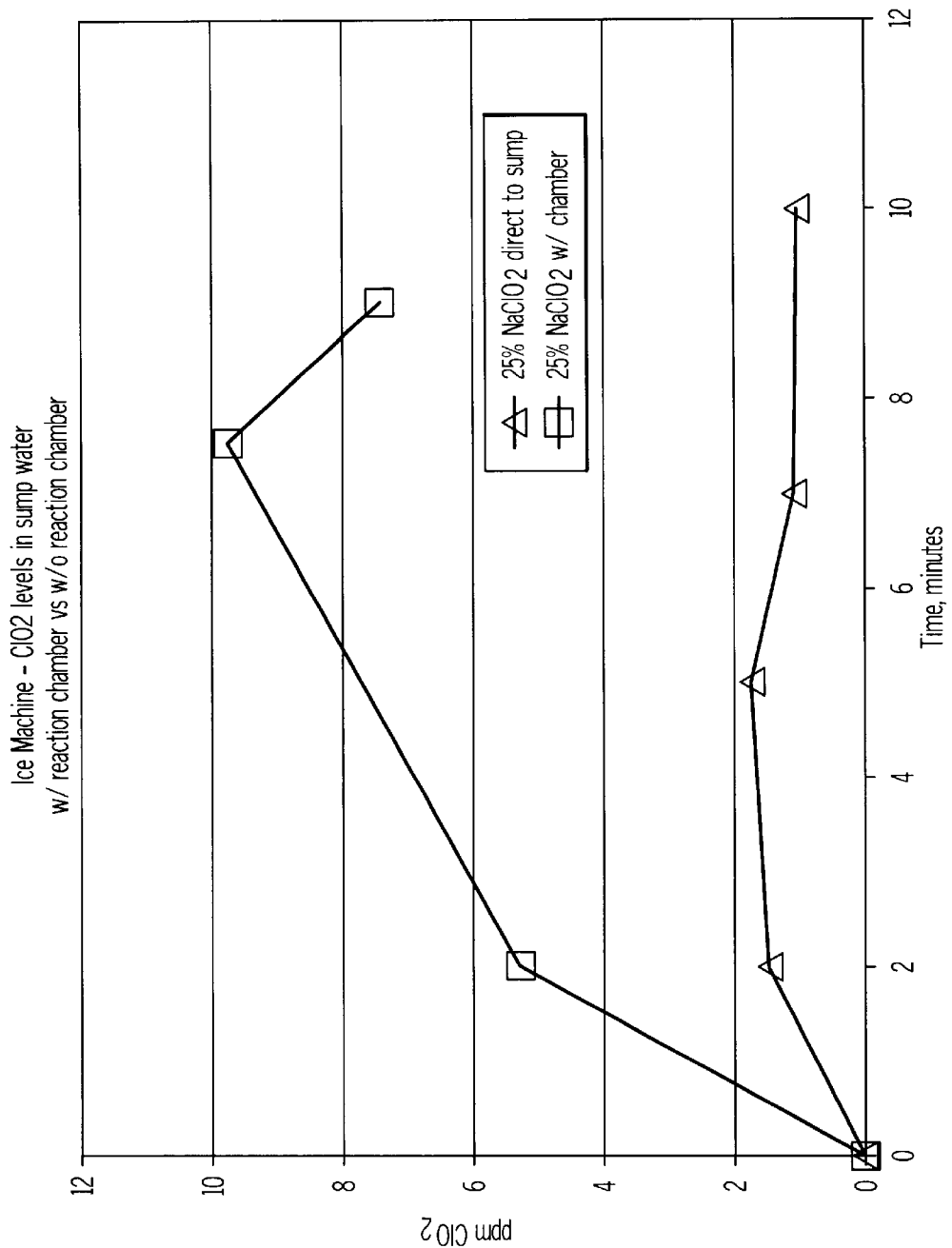
FIG. 11 is a graph showing the concentration of chlorine dioxide in the sump of an ice machine when the reactants are supplied at a higher concentration than FIG. 10 into the sump and into a pre-mix chamber.
Figure 12:
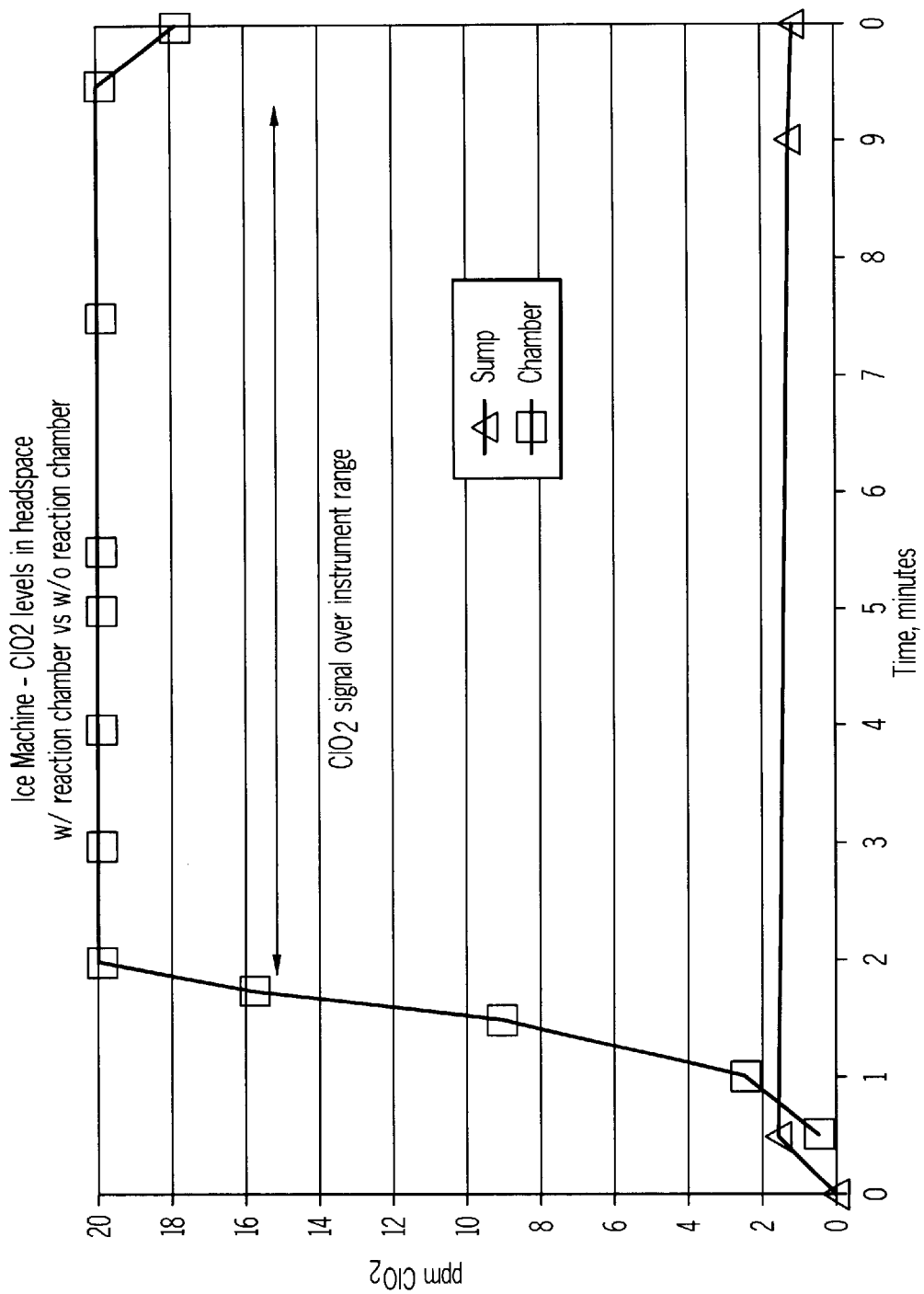
FIG. 12 is a graph showing the concentration of chlorine dioxide in the head space of an ice machine when the reactants are supplied at a higher concentration than FIG. 10 into the sump and into a pre-mix chamber.

LIMEAWAY (95 ml) and a 25% sodium chlorite solution (13 ml) were simultaneously dispensed into an ice machine per the method of Example 2. FIG. 11 shows the concentrations of chlorine dioxide in the sump water when the products are dispensed directly into the sump and when they are pre-mixed. FIG. 12 shows the headspace concentration of chlorine dioxide when the products are dispensed directly into the sump and when they are pre-mixed in the chamber of Example 1. Much higher levels of chlorine dioxide can be achieved in the headspace and in the sump water when the pre-mix chamber is used.

Figure 10:
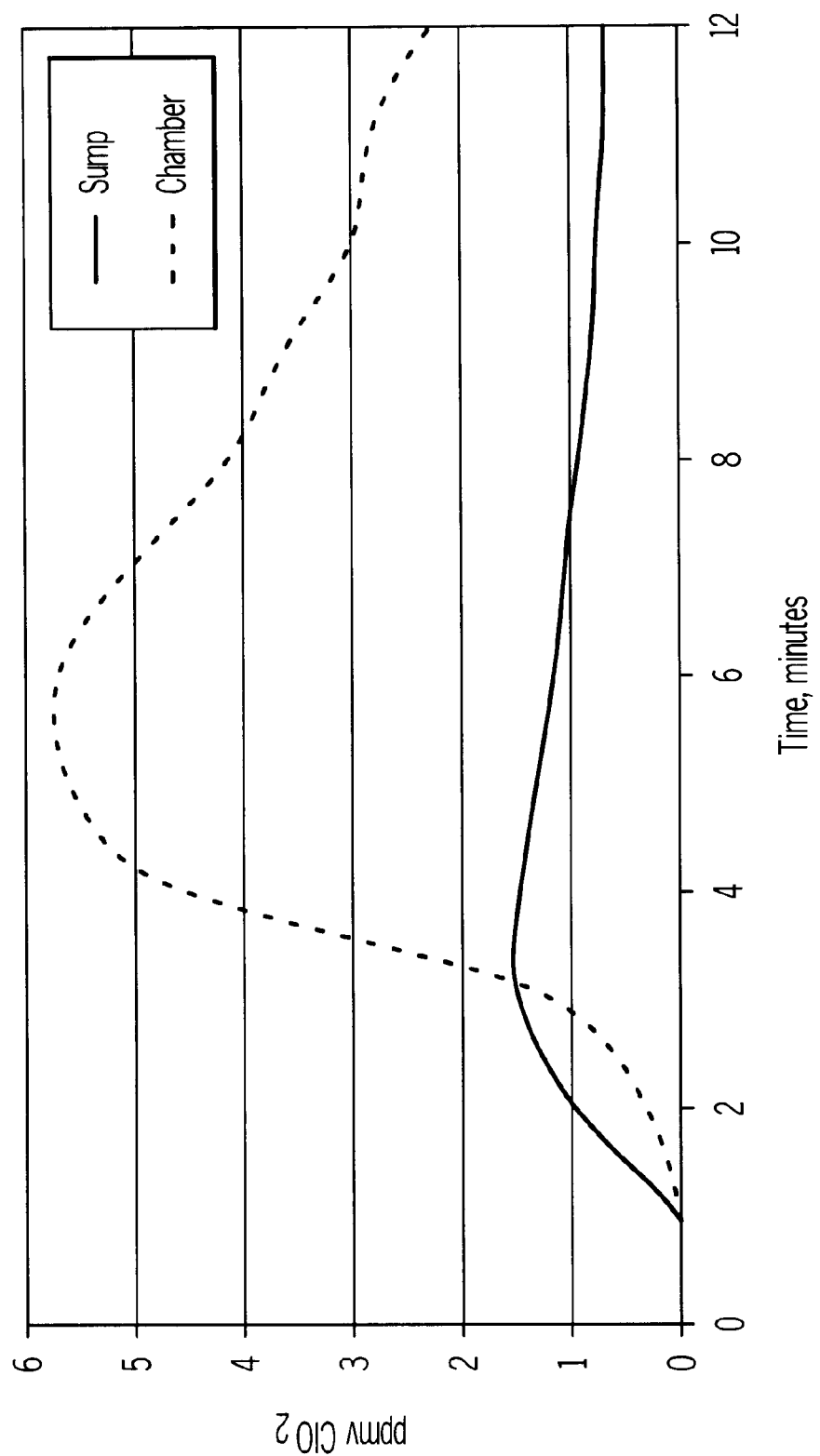
FIG. 10 is a graph showing the concentration of chlorine dioxide in the head space of the ice machine when the reactants are supplied in the sump versus a pre-mix chamber.

A comparison of FIG. 10 and FIG. 11 shows that almost the same level of chlorine dioxide can be generated in the sump water with 6% sodium chlorite solution using the pre-mix chamber as can be generated with an equal volume of 25% sodium chlorite solution without using the premix chamber. In systems with fixed cleaning cycles it is important to be able to manipulate the concentration of chlorine dioxide to a level that creates effective sanitizing.

Recirculation over the evaporator plate promotes effective mass transfer of chlorine dioxide from the liquid into the gas phase which can lead to the production of initially higher levels of chlorine dioxide in the gas phase in some situations when the product is dispensed directly into the sump.

What is claimed is:

1. A deliming and sanitizing process for an ice machine having a water flow system, a sump, an ice bin, and at least one drain, the machine having a headspace within the interior thereof accessible to the interior of the machine, the process comprising, injecting a liquid delimer composition comprising at least one acidic component into the sump, and substantially simultaneously injecting a second sanitizing composition into the sump.

2. The process of claim 1 wherein said liquid delimer composition and said sanitizing composition are injected into a pre-mix reservoir to form a mixture said reservoir having an exit port in fluid communication with said sump.

3. The process of claim 2 wherein said ice machine further comprises an electronic monitoring and control system.

4. The process of claim 3 wherein said electronic monitoring and control system is further equipped with a fail safe system for preventing overflow of said pre-mix reservoir.

5. The process of claim 1 wherein said sanitizing composition comprises a metal chlorite, a metal hypochlorite, a quaternary ammonium compound or peracetic acid.

6. The process of claim 1 wherein said delimer comprises an acidic compound.

7. The process of claim 1 wherein said sanitizing component comprises a metal hypochlorite and said delimer composition comprises an acidic compound and the ratio of said metal hypochlorite to said acidic component is about 1:4 to about 1:15 on a molar basis.

8. The process of claim 1 wherein said sanitizing component comprises a metal hypochlorite and said delimer composition comprises an acidic compound and the ratio of said metal hypochlorite to said acidic component is about 1:5 to about 1:10 on a molar basis.

9. The process of claim 1 wherein injecting step is accomplished by at least one selected from the group consisting of a positive displacement pump, a gear pump, an oscillating pump, a screw pump, a syringe pump, a piston pump or a peristaltic pump.

10. The process of claim 1 wherein said injecting step is accomplished with one dual liquid pumping mechanism.

11. The process of claim 1 wherein said delimer composition comprises at least one member selected from the group consisting of phosphoric acid, sulfuric acid, hydrochloric acid, citric acid, and mixtures thereof.

12. A deliming and sanitizing process for an ice machine having a water flow system, a sump, an ice bin and at least one drain, the machine having a headspace within the interior thereof accessible to the interior of the machine, the process comprising, injecting a liquid delimer composition comprising at least one acidic component into a pre-mix reservoir which is in fluid communication with the sump, and substantially simultaneously injecting a liquid sanitizer composition into said pre-mix reservoir.

wherein said pre-mix reservoir is in fluid communication with said sump and said sump is in fluid communication with said water flow system.

13. The process of claim 12 wherein said liquid delimer is an acidic delimer and said sanitizing composition is sodium chlorite or sodium hypochlorite.

14. An automatic ice-making machine comprising:
a) a water flow system;
b) a sump;
c) an ice bin;
c) at least one drain; and
d) an automatic cleaning system comprising a dual liquid injecting mechanism for injecting a first liquid delimer composition and a second liquid sanitizer composition, and a pre-mix reservoir wherein each of a predetermined amount of said first liquid delimer composition and said second liquid sanitizer composition are injected into said pre-mix reservoir and upon activation by said automatic cleaning system are injected into said water flow system of said ice making machine.

15. The automatic ice-making machine of claim 14 wherein said reservoir is in fluid communication with said sump.

16. The automatic ice-making machine of claim 14 wherein said ice making machine has a single drain for the ice bin and the sump.

17. The automatic ice making machine of claim 14 wherein said first liquid is an acidic delimer composition.

18. The automatic ice making machine of claim 14 wherein said first liquid is an acidic delimer composition and said second liquid is a metal chlorite or a metal hypochlorite composition.

19. The automatic ice making machine of claim 18 wherein chlorine dioxide is present in said pre-mix reservoir, in said sump and in said head space of said ice making machine.

20. The automatic ice making machine of claim 14 wherein said second liquid is a metal chlorite composition, a metal hypochlorite composition, a quaternary ammonium composition or a peracetic acid composition.

21. The automatic ice making machine of claim 14 wherein said dual injecting mechanism is a positive displacement pump, a gear pump, an oscillating pump, a screw pump, a syringe pump, a piston pump or a peristaltic pump.

* * * * *